United States Patent [19]

Seed

[11] 4,286,964

[45] Sep. 1, 1981

[54] POLYFUNCTIONAL EPOXIDES AND HALOHYDRINS USED AS BRIDGING GROUPS TO BIND AROMATIC AMINE GROUP-CONTAINING ALCOHOLS AND THIOLS TO HYDROXYL BEARING SUBSTRATES

[76] Inventor: Brian S. Seed, 40 Graham Rd., Scarsdale, N.Y. 10583

[21] Appl. No.: 84,509

[22] Filed: Oct. 12, 1979

[51] Int. Cl.$^3$ .................. C08B 11/20; C08B 15/06; G01N 31/22; G01N 33/16

[52] U.S. Cl. ........................... 23/230 B; 8/181; 8/666; 8/DIG. 8; 23/230.3; 23/902; 422/71; 424/1; 424/1.5; 424/12; 435/6; 435/172; 536/43; 536/85

[58] Field of Search .............. 536/43, 85; 8/DIG. 8; 422/71; 23/230 B, 230.3; 424/1, 1.5, 12; 435/6, 172

[56] References Cited

U.S. PATENT DOCUMENTS

| | | | |
|---|---|---|---|
| 3,464,781 | 9/1969 | Berni et al. | 536/43 |
| 4,139,346 | 2/1979 | Rabbani | 23/230 B |
| 4,200,735 | 4/1980 | Sano et al. | 536/43 |

OTHER PUBLICATIONS

McKelvey et al., *J. of Polymer Sci.*, vol. 11, pp. 1693–1701, (1967).

Primary Examiner—James C. Cannon
Attorney, Agent, or Firm—Christie, Parker & Hale

[57] ABSTRACT

A process for preparing a derivative of an hydroxyl bearing substrate by reacting an hydroxyl bearing substrate with oxirane bearing molecules to produce an oxirane ring bearing substrate; and reacting the oxirane ring with a substituted primary aromatic amine selected from primary aromatic amine alcohols and primary aromatic amine thiols. Among the compositions so produced is a stable modified hydroxyl bearing substrate or hydroxyl bearing sheet having covalently bonded thereto primary aromatic amines which can be diazotized. The diazotized substrate selectively, covalently binds proteins, polypeptides, peptides, nucleic acids, RNA, single stranded DNA, and nucleic acid hybrids.

33 Claims, No Drawings

POLYFUNCTIONAL EPOXIDES AND HALOHYDRINS USED AS BRIDGING GROUPS TO BIND AROMATIC AMINE GROUP-CONTAINING ALCOHOLS AND THIOLS TO HYDROXYL BEARING SUBSTRATES

BACKGROUND OF THE INVENTION

The present invention relates to a new class of hydroxylic substrate bearing primary aromatic amine or diazo groups which can be used to bind nucleic acids, proteins, or other biological molecules functionally capable of reacting with diazotized primary amine groups, and various methods of preparation of such modified substrates.

The reactions of nucleic acids and proteins with cellulose papers modified with diazotized m-aminobenzyloxymethyl groups and some uses of such reactions have been described in a series of publications by Stark and collaborators in *Cell* 5, 301-310 (1975). *Proc. Natl. Acad. Sci. U.S.A.* 74, 5350-5354 (1977), *Biochem Biophys. Res. Commun.* 85, 1104-1112 (1978), *Proc. Natl. Acad. Sci. U.S.A.* 76, 3116-3120 (1979), and *Proc. Natl. Acad. Sci. U.S.A.* 76, 3683-3687 (1979). A paper modified with m-aminobenzyloxymethyl groups for the above purposes has been described by Rabbani, U.S. Pat. No. 4,139,346, Feb. 13, 1979.

The methods of Stark and collaborators and Rabbani rely upon a technology developed by Kursanov and Solodkov in *J. Applied Chem. (U.S.S.R.)* 16, 351-355 (1943) for the synthesis of m-nitrobenzyloxymethyl pyridinium chloride (NBPC), and its subsequent coupling to cotton fabric to secure an m-nitrobenzyloxymethyl derivative of cellulose. The m-nitrobenzyloxymethyl cellulose was reduced to the m-aminobenzyloxymethyl derivative, diazotized, and coupled to 2-napthol to afford a covalently dyed, red-colored fabric.

The advances of Stark and collaborators were (1) to demonstrate that the technology of Kursanov and Solodkov could be applied to couple nucleic acids and proteins to cellulose papers; and (2) specifically, to use such cellulose papers to immobilize patterns of nucleic acids and proteins in a form amenable to subsequent identification and analysis.

The Kursanov-Solodkov process, and its product, have several undesirable features. The NBPC reagent is expensive and difficult to obtain. The m-aminobenzyloxymethyl derivative of cellulose is unstable, and is best prepared just prior to use, a step which entails a tedious reduction and washing. Hence, it was an object of the present invention to devise a simple, economical synthesis of a stable paper substituted with aromatic primary amine or diazo groups.

SUMMARY OF THE INVENTION

The process herein relates to for preparing a derivative of an hydroxyl bearing substrate. An hydroxyl bearing substrate is reacted with oxirane bearing molecules to produce an oxirane ring bearing substrate. The oxirane ring bearing substrate is subsequently reacted with a substituted primary aromatic amine selected from the group consisting of primary aromatic amine alcohols and primary aromatic amine thiols. Among the compositions so produced is a stable modified hydroxyl bearing substrate comprising substituted phenyl thioether groups having structural units having the general formula:

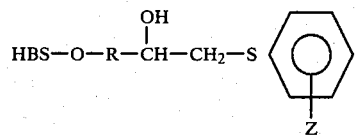

in which HBS is the hydroxyl bearing substrate, R is selected from the group consisting of alkyl groups, hydroxyl bearing alkyl groups, aryl groups, alkylaryl groups, alkyl ether groups, hydroxyl bearing alkyl ether groups, aryl ether groups, alkylaryl ether groups, and hydroxyl bearing alkylaryl ether groups; and in which Z is selected from the group consisting of primary amines, diazo chlorides, diazo fluoborates, and diazo fluorophosphates. Alkyl ethers, hydroxyl bearing alkyl ethers, and aryl ethers as used herein include alkyl polyethers, hydroxyl bearing alkyl polyethers, and aryl polyethers.

Another composition so produced is a stable modified hydroxyl bearing sheet comprising substituted phenyl groups having structural units having the general formula:

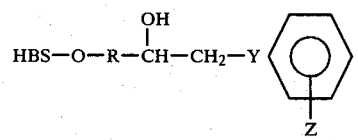

in which HBS is the hydroxyl bearing substrate, R is selected from the group consisting of alkyl groups, hydroxyl bearing groups, aryl groups, alkylaryl groups, alkyl ether groups, hydroxyl bearing alkyl ether groups, aryl ether groups, alkylaryl ether groups, and hydroxyl bearing alkylaryl ether groups; Z is selected from the group consisting of primary amines, diazo chlorides, diazo fluoborates, and diazo fluorophosphates, and Y is selected from the group consisting of oxygen and sulfur.

DETAILED DESCRIPTION

The invention is based on a sequence of two reactions. In the first step, an hydroxyl bearing support, such as a cellulose paper or other hydroxyl bearing sheet, cellulose fiber or crystal, agarose bead, or dextran bead, is substituted with oxirane groups. In the second step, the oxirane activated support is coupled to a primary aromatic amine alcohol or thiol, without prior protection of the amine group. The use of an unprotected amine greatly simplifies the synthesis of the invention because fewer steps are required. Derivatives so produced have been found to have a surprisingly high and useful degree of stability.

The reaction sequence for the first step may be diagrammed as follows:

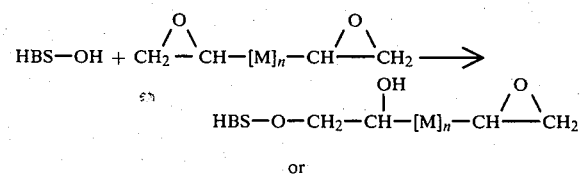

or

-continued

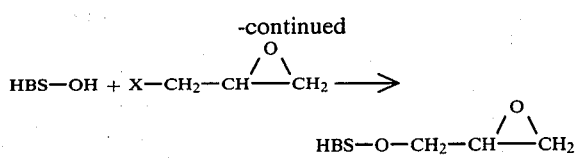

where HBS—OH is the hydroxyl bearing support. M is a connecting group such as a saturated or unsaturated alkyl group, hydroxyl bearing alkyl group, aryl group, ether group, thioether group, amine group, disulphide group, or peptide group, or any combination of such groups, and n is either 0 or 1. When n=0 the oxirane groups are directly linked. X is a halogen, such as chlorine, bromine, or iodine.

Known processes for the introduction of oxirane groups onto similar hydroxyl bearing supports may be used, for example the methods of Nishikawa and Bailon, *Journal of Solid-Phase Biochemistry* 1, 33-49 (1976), Hjerten et al *J. Chromatog.* 101, 281-288 (1974), Sundberg and Porath, *J. Chromatog.* 90, 82-98 (1974), or Porath and Larsson, *J. Chromatog.* 155, 47-68 (1978), as applied to dextran or agarose beads.

The second step may be schematically represented as follows:

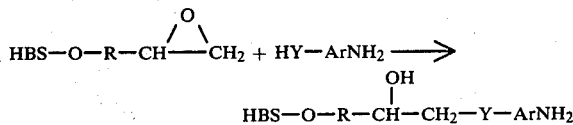

where R represents the linkage resulting from the first step, Y represents an oxygen or a sulfur, and ArNH$_2$ represents an aromatic primary amine group. The primary amine group of the derivatized support may be converted to a diazo group by treatment with acidic sodium nitrite solution by the known process. The diazo group may be stabilized as the salt of a weakly nucleophilic anion such as the fluoborate or hexafluorophosphate anions.

A preferred method used for the first step is the condensation of the hydroxyl group of the support medium and a bisoxirane, such as 1,4-butanediol diglycidyl ether (BDG), in either aqueous or non-aqueous sodium hydroxide solution. Acetone and alcohols including methanol and ethanol are preferred non-aqueous solvents. An alternative method for the first step includes the condensation of the epihalohydrins, preferably epibromohydrin or epichlorohydrin, in either aqueous or non-aqueous sodium hydroxide solution, or in condensation with a non-aqueous boron trifluoride solution followed by aqueous sodium hydroxide solution.

In aqueous solution, the concentration of sodium hydroxide is approximately 0.25 to 0.5 molar, while in non-aqueous solution the concentration of sodium hydroxide is approximately 0.05 to 0.1 molar. The reaction in non-aqueous solution yields lower degrees of substitution, but allows the oxirane-bearing reagent to be dissolved in higher concentrations than possible in an aqueous medium. The increased solubility of oxirane bearing reagent in non-aqueous medium consequently permits coupling to proceed with less rigorous agitation than in aqueous solution. Typical condensation times for the BDG reaction range from 8 to 16 hours, preferably around 10 hours. Reactions with epibromohydrin require about four-fold less reagent by volume than reactions with the BDG reagent for equivalent substitution. However, the BDG process produces an activated support bearing an oxirane group on a longer side chain than does the epibromohydrin process, and some derivatives of cellulose supports activated by the BDG process bind nucleic acids more efficiently than those derivatives activated by the epibromohydrin process. Condensation of epihalohydrins with the support can also be performed in a non-hydroxylic solvent such as acetone or dioxane, containing catalytic amounts such as 2% by volume of boron trifluoride ether complex. This reaction proceeds very rapidly in less than one hour. However, the reaction generally yields a fairly low degree of substitution in the final product.

All of the alkaline aqueous coupling procedures detailed above demand a high degree of agitation. This can be accomplished advantageously by an end-over-end tumbling of the support to be derivatized, for example, in a solvent-stable reaction vessel or plastic bag. The non-aqueous alkaline and boron trifluoride synthesis do not require the same high degree of agitation.

In the second reaction step the oxirane derivatized support is coupled to an aromatic primary amine alcohol or thiol such as an aminophenol or an aminothiophenol, in alkaline solvent, for example alkaline ethanol, methanol or acetone solutions. Although in principle both aromatic primary amine moiety and the aromatic alcohol or thiol moiety might be expected to react with the oxirane group, the rate of reaction of the oxirane with the primary amine is generally sufficiently low under these conditions to eliminate the need for protection of the primary amine. The coupling reaction can be performed in several ways, for example by draining off the excess oxirane reagent of the first step, and adding the aromatic primary amine reagent dissolved in solvent directly to the reaction vessel containing the epoxide support, or by washing the oxirane reagent out of the support with alkaline solvent, for example a solution comprising one part alcohol and one part 0.5 M NaOH, and then adding to the washed support a solution of the aromatic primary amine alcohol or thiol dissolved in the same alkaline solvent. The aromatic amine thiols couple very rapidly under the latter conditions, the reaction being complete in less than one hour. Aromatic alcohols take longer to couple, and are generally allowed to react for 12 to 24 hours.

After the reaction with the aromatic primary amine reagent, the support can be washed to remove the remaining reagent, for example with sequential washes of an alcohol and an acidic aqueous solution, such as methanol or ethanol ethanol and 0.1 N HCl; or by sequential washes with an aqueous basic reducing solution and an acidic solution, such as 0.05 N NaOH containing 0.25 mg/ml NaBH$_4$, and 0.1 N HCl. The final wash should be acidic. After the final wash the support may be rinsed extensively in distilled water, and soaked in acidic solution and/or dried. An alcohol or other volatile non-aqueous solvent may be added to accelerate drying. Drying may be carried out at elevated temperature, for example 60°, but preferably in the absence of light, to prevent oxidation of the aromatic primary amine groups.

The aromatic primary amine-substituted support may be diazotized with HCl and NaNO$_2$ by standard procedures. The diazotized form may be stabilized in a number of ways, for example by conversion to the salt of a weakly nucleophilic anion, such as the tetrafluoborate (BF$_4^-$) or hexafluorophosphate (PF$_6^-$) anions, in acidic solution, such as 1 N HCl; or by conversion to the diazoacetate in glacial acetic acid. The stabilized diazotized support may be recovered by washing with a non-aqueous volatile solvent, such as an alcohol, and drying. The stabilized diazo forms retain reactivity for from several days to many months, depending upon the amine substituent; but must be kept cool and dry and protected from light.

The following examples illustrate the preparation of aromatic amine cellulose papers and their diazo derivatives.

EXAMPLE 1

20 g. of cellulose paper were placed in a heat-sealable polyester bag and 70 ml 0.5 N NaOH added, followed by 30 ml BDG. The bag was sealed shut with a commercial sealer and rotated end-over-end at 30 rpm for 10 hours. The fluid was poured off and the papers soaked in 500 ml of a solution comprising one part ethanol and one part 0.5 N NaOH, with mild agitation to remove the BDG. The papers were then soaked in a one percent solution of 2-aminothiophenol formed by dissolving the aminothiophenol to 2% in ethanol, and adding an equal volume of 0.5 N NaOH. The papers were steeped in the 1% aminothiophenol solution for one hour, then washed in the sequence of ethanol followed by 0.1 N HCl twice; then washed again with distilled water. The final product was washed with ethanol and dried at 60° in the dark.

EXAMPLE 2

20 g. of cellulose paper was placed in a polyester bag, followed by 92 ml of 0.5 N NaOH and 8 ml of epibromohydrin. The bag was sealed shut and rotated end-over-end for 4 hours. The fluid was then poured off and 40 ml acetone containing 10 ml 2-aminothiophenol added to the bag. The bag was resealed and rotated another 12 hours. The contents were removed and washed in acetone followed by 0.1 N HCl twice, then distilled water, 0.1 N HCl and distilled water as in Example 1. The final product was dried at room temperature.

EXAMPLE 3

The procedures of Example 1 were reproduced in all material detail with the exception that the epibromohydrin was poured off, a mixture of 10 g. 4-aminophenyldisulfide, 1 g $NaBH_4$ and 40 ml ethanol were added in place of the 2-aminothiophenol-acetone mixture.

EXAMPLE 4

The procedures of Example 1 were reproduced in all material detail with the exception that the diglycidyl ether was poured off, the aminophenyldisulfide mixture of Example 3 was added, the bag resealed, and rotated another 12 hours. The contents were then removed and washed as in Example 2, but with several additional acetone washes.

EXAMPLE 5

The procedures of Example 4 were reproduced in all material detail with the exception that a mixture of 10 g 3-nitrophenyl disulfide, 1 g $NaBH_4$ and 40 ml ethanol. The final product was the m-nitrophenyl thioether derivative, which was reduced with 20% w/v sodium dithionite solution at 60° for one hour, followed by extensive washing in 0.1 N HCl, a rinse with distilled water, and drying.

EXAMPLE 6

The procedures of Example 4 were reproduced in all material detail with the exception that a mixture of 10 g of 2-aminophenol and 40 ml acetone was added after the diglycidyl ether was poured off.

EXAMPLE 7

The procedures of Example 4 were reproduced in all material detail with the exception that a mixture of 10 g of 3-aminophenol and 40 ml acetone was added after the diglycidyl ether was poured off.

EXAMPLE 8

The procedures of Example 4 were reproduced in all material detail with the exception that a mixture of 10 g of 4-aminophenol and 40 ml acetone was added after the diglycidyl ether was poured off.

EXAMPLE 9

The procedures of Example 4 were reproduced in all material detail with the exception that a mixture of 10 g of 4-aminosalicylic acid and 40 ml ethanol was added after the diglycidyl ether was poured off.

EXAMPLE 10

The procedures of Examples 4 were reproduced in all material detail with the exception that a mixture of 10 g of 5-chloro-2-hydroxyaniline and 40 ml acetone was added after the diglycidyl ether was poured off.

EXAMPLE 11

Derivatized cellulose papers of the 10 preceding examples were diazotized in 1.2 N HCl containing 250 micrograms per ml of sodium nitrite on ice for one hour. The presence of diazo groups was affirmed by adding the papers to a solution of 2-naphthol in 1% sodium tetraborate decahydrate. The aminophenyl thioether papers yield orange-red to deep red papers, the various aminophenyl ethers pink to pale pink azo adducts. The 4-aminophenol adduct yields a green derivative.

EXAMPLE 12

Papers diazotized in Example 11 were soaked in a 1% solution of $NaBF_4$ or $NaPF_6$ in 1.2 M HCl for 10 minutes, washed with ethanol, acetone, and dried. The 4-diazophenyl thioether of epibromohydrin activated paper was stable for months at room temperature, the 2-diazophenyl thioether of bisoxirane activated paper was stable for more than a week. When stored in the cold ($-20°$), the 2-diazophenylthioether of bisoxirane activated paper was stable for more than 9 months.

EXAMPLE 13

To demonstrate the nucleic acid binding capability of the various diazotized cellulose derivatives, phosphorous-32 isotope-labelled DNA derived from the plasmid pBR322 was digested with a restriction endonuclease isolated from *Arthrobacter luteus* (the Alu I nuclease) in order to generate a discrete set of DNA fragments ranging in size from 910 to 11 base pairs. The resulting DNA fragments were separated according to molecular weight by electrophoresis through a 2.5% w/v agarose gel. The DNA fragments in the gel were rendered single-stranded by exposure to alkali and transferred by elution to strips of paper diazotized by the method of Example 11. Transfer was performed in citrate-phosphate or acetate buffer at pH 4.0, by the known process.

Transfer was quantitated by scintillation counting of the strips of diazotized paper. The fraction of DNA retained by the various papers was as follows:

| Example | % Retained on Paper |
|---------|---------------------|
| 1 | 57.0 |
| 2 | 51.0 |
| 3 | 27.0 |
| 4 | 4.8 |
| 5 | 4.5 |
| 6 | 1.7 |
| 7 | 0.6 |
| 8 | 49.0 |
| 9 | 1.1 |
| 10 | 1.5 |

What is claimed is:

1. A stable modified hydroxyl bearing substrate comprising substituted phenyl thioether groups having structural units having the general formula:

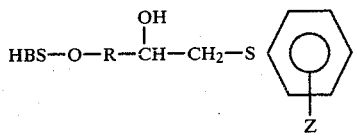

in which HBS comprises a hydroxyl bearing substrate, R is selected from the group consisting of alkyl groups, hydroxyl bearing alkyl groups, aryl groups, alkylaryl groups, alkyl ether groups, hydroxyl bearing alkyl ether groups, aryl ether groups, alkylaryl ether groups, and hydroxyl bearing alkylaryl ether groups; and in which Z is selected from the group consisting of primary amines, diazo chlorides, diazo fluoborates, and diazo fluorophosphates.

2. The modified hydroxyl bearing substrate of claim 1 in which R comprises a methylene group.

3. The modified hydroxyl bearing substrate of claim 1 in which R comprises a group having the formula

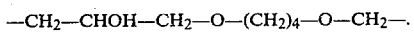

4. A stable modified hydroxyl bearing sheet comprising substituted phenyl groups having structural units having the general formula:

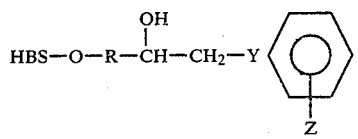

in which HBS comprises a hydroxyl bearing substrate, R is selected from the group consisting of alkyl groups, hydroxyl bearing groups, aryl groups, alkylaryl groups, alkyl ether groups, hydroxyl bearing alkyl ether groups, aryl ether groups, alkylaryl ether groups, and hydroxyl bearing alkylaryl ether groups; Y is selected from the group consisting of oxygen and sulfur; and in which Z is selected from the group consisting of primary amines, diazo chlorides, diazo fluoborates, and diazo fluorophosphates.

5. The modified hydroxyl bearing sheet of claim 4 in which R comprises a methylene group.

6. The modified hydroxyl bearing sheet of claim 4 in which R comprises a group having the formula

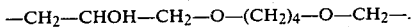

7. The modified sheet of claim 4 wherein the sheet is comprised of cellulose paper.

8. The modified sheet of claim 5 in which the sheet is comprised of cellulose paper.

9. The modified sheet of claim 6 in which the sheet is comprised of cellulose paper.

10. A process for preparing a derivative of a hydroxyl bearing substrate comprising the steps of:
reacting a hydroxyl bearing substrate with oxirane bearing molecules to produce an oxirane ring bearing substrate; and
reacting the oxirane ring bearing substrate with a substituted primary aromatic amine selected from the group consisting of primary aromatic amine alcohols and primary aromatic amine thiols.

11. The method of claim 10 wherein the hydroxyl bearing substrate is comprised of an hydroxyl bearing sheet.

12. The method of claim 10 wherein the hydroxyl bearing substrate is comprised of a cellulose paper.

13. The method of claim 10 wherein the oxirane bearing molecule has a structure having the general formula:

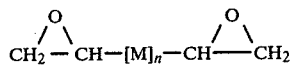

in which M is selected from the group consisting of alkyl groups, aryl groups, ether groups, alkyl ether groups, alkyl aryl groups and alkyl aryl ether groups, and n is an integer selected from the group consisting of 0 and 1.

14. The method of claim 10 wherein the oxirane bearing molecule has a structure having the general formula:

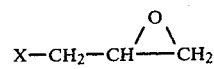

in which X represents a halogen selected from the group comprising chlorine, bromine, and iodine.

15. The method of claim 10 wherein the oxirane bearing molecule is 1,4-butanediol diglycidyl ether.

16. The method of claim 13 wherein the hydroxyl bearing substrate is comprised of an hydroxyl bearing sheet.

17. The method of claim 13 wherein the hydroxyl bearing substrate is comprised of a cellulose paper.

18. The method of claim 14 wherein the hydroxyl bearing substrate is comprised of an hydroxyl bearing sheet.

19. The method of claim 14 wherein the hydroxyl bearing substrate is comprised of a cellulose paper.

20. The method of claim 11 wherein the oxirane bearing molecule is 1,4-butanediol diglycidyl ether.

21. The method of claim 12 wherein the oxirane bearing molecule is 1,4-butanedioldiglycidyl ether.

22. The method of claim 10 wherein the substituted primary aromatic amine is selected from the group consisting of o-aminophenol, m-aminophenol, p-aminophenol, o-aminothiophenol, m-aminothiolphenol, and p-aminothiophenol.

23. The method of claim 22 wherein the hydroxyl bearing substrate is comprised of an hydroxyl bearing sheet.

24. The method of claim 22 wherein the hydroxyl bearing substrate is comprised of a cellulose paper.

25. The method of claim 22 wherein the oxirane bearing molecule is 1,4-butanediol diglycidyl ether.

26. The method of claims 14, 15, 16, 17, 18, 19, 20, or 21 wherein the substituted primary aromatic amine is selected from the group consisting of o-aminophenol, m-aminophenol, p-aminophenol, o-aminothiophenol, m-aminothiophenol, and p-aminothiophenol.

27. The method of claims 10, 11, 12, 13, 14, 15, 16, 17, 18, 19, 20, 21, 22, 23, 24, or 25 comprising the additional steps of diazotizing the primary amine by reaction with a member selected from the group consisting of nitrous acid and acidic solution of sodium nitrite; and stabilizing the diazo groups by conversion in acidic solution to the salt of a weakly nucleophilic anion selected from the group consisting of tetrafluoborate and hexafluorophosphate.

28. The method of claims 11 or 12 wherein the step of covalently bonding the oxirane bearing molecule to the hydroxyl bearing substrate is conducted in a basic aqueous medium.

29. The method of claim 28 wherein the step of covalently bonding the oxirane bearing molecule to the hydroxyl bearing substrate is conducted by vigorous end-over-end agitation.

30. The method of claims 10, 11 or 12 wherein the step of covalently bonding the oxirane bearing molecule to the hydroxyl bearing substrate is conducted in basic nonaqueous medium.

31. The method of claim 30 wherein the basic nonaqueous medium comprises a solution of from 0.05 to 0.1 N NaOH in a solvent selected from the group consisting of methanol, ethanol and acetone.

32. A process for preparing a derivative of an hydroxyl bearing substrate comprising the step of covalently binding a diazotized, modified hydroxyl bearing substrate of claims 1, 4, 7, 8, or 9 with proteins, polypeptides, peptides, nucleic acids, RNA, single stranded DNA, or nucleic acid hybrids.

33. The modified substrate of claims 1 or 4 wherein the diazotized amine is selectively covalently bound to molecules selected from the group consisting of proteins, polypeptides, peptides, nucleic acids, RNA, single stranded DNA and nucleic acid hybrids.

* * * * *